United States Patent
Stergiopulos

(10) Patent No.: US 6,641,605 B1
(45) Date of Patent: Nov. 4, 2003

(54) IMPLANT WITH DEFLECTOR FOR INTRAVASCULAR DILATION

(75) Inventor: Nikolaos Stergiopulos, Saint Sulpice (CH)

(73) Assignee: Ecole Polytechnique Federale de la Lausanne, Lausanne (CH)

(*) Notice: Subject to any disclaimer, the term of this patent is extended or adjusted under 35 U.S.C. 154(b) by 0 days.

(21) Appl. No.: 09/446,355

(22) PCT Filed: Jun. 19, 1998

(86) PCT No.: PCT/IB98/00948
§ 371 (c)(1),
(2), (4) Date: Dec. 20, 1999

(87) PCT Pub. No.: WO98/58599
PCT Pub. Date: Dec. 30, 1998

(30) Foreign Application Priority Data

Jun. 20, 1997 (CH) .................................. 1514/97

(51) Int. Cl.[7] .................................. A61F 2/06
(52) U.S. Cl. .................. 623/1.1; 606/200; 623/1.1
(58) Field of Search ............... 623/1.14, 1.16, 623/1.2, 1.22, 1.27, 1.36, 1.15, 1.1, 1.18, 1.21, 1.12; 606/194, 195, 200

(56) References Cited

U.S. PATENT DOCUMENTS

| 3,868,956 | A | | 3/1975 | Alfidi et al. | |
|---|---|---|---|---|---|
| 4,768,507 | A | * | 9/1988 | Fischell et al. | 606/108 |
| 5,129,910 | A | | 7/1992 | Phan et al. | |
| 5,290,305 | A | * | 3/1994 | Inoue | 623/1.2 |
| 5,304,194 | A | | 4/1994 | Chee et al. | |
| 5,370,657 | A | * | 12/1994 | Irie | 606/200 |
| 5,378,234 | A | * | 1/1995 | Hammerslag et al. | 600/528 |
| 5,573,547 | A | | 11/1996 | LeVeen et al. | |
| 5,855,597 | A | * | 1/1999 | Jayaraman | 623/1.16 |
| 5,871,436 | A | * | 2/1999 | Eury | 600/3 |
| 5,938,695 | A | * | 8/1999 | Borghi | 623/1.16 |
| 6,071,305 | A | * | 6/2000 | Brown et al. | 623/1.43 |
| 6,187,027 | B1 | * | 2/2001 | Mariant et al. | 606/191 |

FOREIGN PATENT DOCUMENTS

| EP | 0 433 011 | 6/1991 |
|---|---|---|
| EP | 0 722 700 | 7/1996 |
| WO | WO 93/01764 | 2/1993 |

* cited by examiner

Primary Examiner—Bruce Snow
Assistant Examiner—Brian E Pellegrino
(74) Attorney, Agent, or Firm—Young & Thompson

(57) ABSTRACT

An intravascular dilator includes a central body acting as deflector o the blood flow to increase the value of shear stress to the artery wall. Flexible spires soldered to the deflector are radially extensible from a first diameter substantially equal to the deflector diameter to a second diameter greater than the artery diameter, the spires rest against the artery internal wall in operative position.

18 Claims, 2 Drawing Sheets

IMPLANT WITH DEFLECTOR FOR INTRAVASCULAR DILATION

BACKGROUND OF THE INVENTION

The present invention relates to an intravascular implant permitting radial dilatation of the arterial walls. These implants or dilatators are known as "stents" in the field of transluminal angioplasty. Transluminal angioplasty consists in treating diseased regions of the arterial system by the introduction of apparatus, particularly catheters, along natural routes. This permits localized intervention without having to have recourse to conventional surgical interventions which have, because of their seriousness, numerous drawbacks for the patients. This technique is particularly used when a constriction or stenosis of the arteries is diagnosed. There is then introduced through the femoral artery a catheter provided at its distal end with an inflatable angioplasty balloon. This catheter is then pushed and guided, with radioscopic monitoring, through the arterial system to the diseased region of the artery. Once this region is reached, the balloon is inflated to dilate the constricted region of the artery. This operation is repeated until it is determined, with the help of the radioscopic monitoring means, that the artery again has a diameter sufficient to ensure an acceptable blood flow. These interventions however have certain drawbacks. Thus, clinical observations show that in about a third of the cases treated, the artery again retracts over a period of time comprised between several days and several months. This phenomenon, which is called "restenosis", requires a new intervention in the diseased artery either by the same method, or by more serious surgical techniques.

DESCRIPTION OF THE RELATED ART

In an effort to solve this problem, it has been proposed to implant permanently in the artery dilatators or "stents" to avoid repeated contraction. These implants usually have a tubular structure open at its ends so as not to disturb the blood flow. These devices, independently of their particular structures, generally have the following characteristics: they are radially extensible from a first diameter, permitting their introduction into the artery with the help of a catheter, to a second larger diameter corresponding substantially to the diameter of the artery. After dilatation of the artery, they are implanted in this latter and bear against the internal wall of the artery, thereby preventing, by a mechanical action, a new constriction of the artery. Once implanted, these stents have a certain resistance to radial compression and thus maintain the artery open whilst permitting blood flow. In practice, stents of two different types are used at present. The first are deformed by inflation of a balloon during their emplacement; the second stents are so-called auto-extensible. The auto-extensible stents do not require external mechanical action to pass from a first diameter during introduction, to a second larger diameter in the service position. This effect is obtained either by the use of material having a shape memory, such as Nitinol (trademark), or by a spring effect. There has also been proposed, for example by European patent EP-433 011 B1, a stent which comprises a radioactive isotope which tends to decrease the phenomenon of restenosis by radiotherapy. In other embodiments, the surface of the stent, in contact with the internal wall of the artery or the vessel, has a suitable surface treatment permitting the local distribution of antithrombogenetic chemical substances.

These devices, although having contributed to the decrease in the rate of restenosis, have nevertheless not totally solved the problem. Thus there is seen, in about 22% of the cases treated by angioplasty and the implantation of a stent, a tissue reaction which leads to increase the thickness of the internal layer of the artery. If this phenomenon is not stabilized and continues to increase, the artery becomes plugged again.

SUMMARY OF THE INVENTION

The present invention has for its object to overcome the drawbacks mentioned above, by providing a dilatation implant promoting the decrease in the rate of restenosis, in particular by its action on the internal wall of artery. Another object of the invention consists in the use of such a device to increase the shear stress at the blood/wall interface in an artery or a blood vessel. Finally, the invention also has for its object a process permitting the increase of shear stress at the level of the arterial wall. The stent according to the present invention is distinguished for this purpose by the below.

BRIEF DESCRIPTION OF THE DRAWINGS

The invention will now be described with reference to the accompanying drawings, which show schematically and by way of non-limiting example, one embodiment of an intravascular stent according to the invention.

DETAILED DESCRIPTION OF THE PREFERRED EMBODIMENTS

Scientific studies, confirmed by critical observations, have shown that restenosis is attributed to a cellular proliferation of the intimal tissue, called intimal hyperplasia. The mechanisms of this reaction are not entirely understood at present. However, it is certain that the prevention or reduction of intimal hyperplasia constitutes a key element in the success of the treatment of stenosis or arterial occlusions. It has been determined in animals that intimal hyperplasia is reduced when the blood flow is high in the vessel in question. On the other hand, when this flow rate is low, the intimal layer increases. The same determination has been made by cardiologists and radiologists, who have observed that following an angioplasty, the stents remain open if the flow rate is high and that they have the tendency to plug in the presence of a low blood flow rate. There exists as a result a certain relationship between the blood flow rate and intimal hyperplasia. This fact is confirmed by several medical studies which tend to show that intimal hyperplasia is not a pathological process, but rather an adaptive response of the artery or the vessel which remodels itself so as to maintain or to restore the optimum level of shear stress at the wall.

The passage of blood in an artery creates by friction forces on the internal wall of the artery. When the flow rate is high, the shear stresses are high on the endothelial cells of the artery wall. These forces are on the contrary low in the presence of an insufficient flow. It is moreover known that the shear stress at the internal wall is directly proportional to the flow (Q) and inversely proportional to the cube of the arterial diameter. It results from this that when the perfusion flow rate is low, intimal hyperplasia reduces the diameter of the artery so as to restore the normal value of the stress. If a low flow rate persists, or if progressively diminishes, the normal shear stress cannot be reestablished and intimal hyperplasia continues, leading finally to restenosis. On the contrary, if the flow is sufficient to reestablish a stress level equal or even superior to the normal stress, intimal hyperplasia stops and the artery remains permanently open.

It results from the above determinations that to stop and block intimal hyperplasia, it is necessary to increase locally the shear stress at the wall, particularly when the flow rate is low. The object of the invention is particularly to permit a substantial local increase of the shear stress at the wall.

Figure 1:
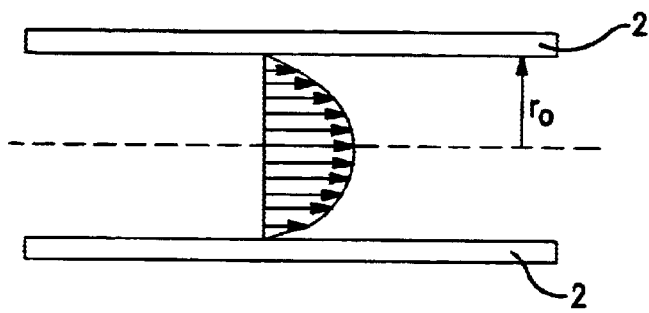
FIG. 1 is a schematic view showing the profile of the speeds in an artery without an implant.
Figure 2:
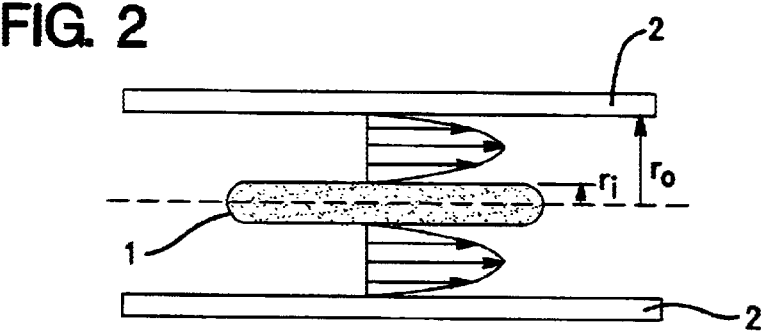
FIG. 2 is a schematic view showing the profile of speeds in an artery having at its center a flow deflector.

Given that the blood flow rate cannot be increased locally, because it is automatically controlled by the organism through resistances which constitute the peripheral vessels, it is necessary as a result to decrease locally the open cross-section of the artery such that the value of the shear stress on the arterial wall increases. To this end, it is proposed to position and to maintain in position, preferably at the center of the artery, at least one body which will act as a deflector of the blood flow on the arterial wall. This flow deflector will thus permit substantially increasing locally the shear stresses on the endophilial cells. FIG. 1 shows schematically the profile of speeds in an artery of radius $r_0$. FIG. 2 shows the same profile of speeds when a flow detector 1 of cylindrical shape is disposed at the center of the artery. The deflector 1 deflects the lines of flow in the radial direction in the direction of the arterial walls 2 and leads to a greater radial gradient of speed adjacent the walls 2 of the artery. Because of this, the shear stress at the blood/wall interface is increased. With reference to FIG. 2, and given the hypothesis that the flow is evolute, the Navier-Stokes equation along the longitudinal axis of symmetry is:

$$\frac{1}{r} \cdot \frac{\partial}{\partial r} \cdot \left(r\frac{\partial u}{\partial r}\right) = -\frac{1}{\mu}\frac{\partial P}{\partial x} \quad \text{where} \tag{1}$$

u is the axial speed,
P the pressure and
$\mu$ the blood viscosity.
By double integration, there is obtained $$u(r) = \frac{1}{4\mu}\frac{\partial P}{\partial x}r^2 + c_1 \ln(r) + c_2 \tag{2}$$

By applying the limit conditions $u(r=r_1)=u(r=r_0)=0$, then by deriving, there is obtained the final expression for the speed distribution $$u(r) = \frac{1}{4\mu}\frac{\partial P}{\partial x}\left[r^2 - r_0^2 + \frac{r_1^2 - r_0^2}{\ln\left(\frac{r_0}{r_1}\right)}\ln\left(\frac{r}{r_i}\right)\right] \tag{3}$$

The flow rate Q can then be calculated by simple integration $$Q = \int_{r_1}^{r_0} u(r)(2\pi r)\,dr = -\frac{\pi}{8\mu}\frac{\partial P}{\partial x}\left[r_0^4 - r_1^4 - \frac{(r_0^2 - r_1^2)^2}{\ln\left(\frac{r_0}{r_1}\right)}\right] \tag{4}$$

The shear stresses acting on the arterial wall $\tau$ are given by $$\tau = -\mu\frac{\partial u}{\partial r}\bigg|_{r=r_0}$$

which by using equation 3 for u(r) becomes (5)

$$\tau = -\frac{1}{4}\frac{\partial P}{\partial x}\left[2r_0 + \frac{1}{r_0}\frac{r_1^2 - r_0^2}{\ln\left(\frac{r_0}{r_1}\right)}\right] \tag{6}$$

Equation 6 can also be expressed as a function of the flow rate Q by using equation 4 for the pressure gradient $$\tau = \frac{2\mu}{\pi}\frac{Q}{r_0^4 - r_1^4 - \frac{(r_0^2 - r_1^2)^2}{\ln\left(\frac{r_0}{r_1}\right)}}\left[2r_0 + \frac{1}{r_0}\frac{r_1^2 - r_0^2}{\ln\left(\frac{r_0}{r_1}\right)}\right] \tag{7}$$

So as better to appreciate the effect of the deflector 1 on the magnitude of shear, this latter is normalized by shear stresses under laminal flow of the Poiseuille type for the same flow as in an open artery. For a flow of the Poiseuille type, it is known that:

$$\tau_{Pois} = \frac{4\mu}{\pi r_0^3}Q \tag{8}$$

There is also obtained the following expression:

$$\frac{\tau}{\tau_{Pois}} = \frac{1}{2}\frac{r_0^3}{r_0^4 - r_1^4 - \frac{(r_0^2 - r_1^2)^2}{\ln\left(\frac{r_0}{r_1}\right)}}\left[2r_0 + \frac{1}{r_0}\frac{r_1^2 - r_0^2}{\ln\left(\frac{r_0}{r_1}\right)}\right] \tag{9}$$

It is thus possible to define the ratio of the deflector/artery radii as a parameter $$\gamma = \frac{r_1}{r_0},$$

to reformulate equation 9 in a non-dimensional form:

$$\frac{\tau}{\tau_{Pois}} = \frac{1 + \frac{\gamma^2 - 1}{2\ln(\gamma)}}{1 - \gamma^4 - \frac{(1 - \gamma^2)^2}{\ln\left(\frac{1}{\gamma}\right)}} \tag{10}$$

Figure 3:
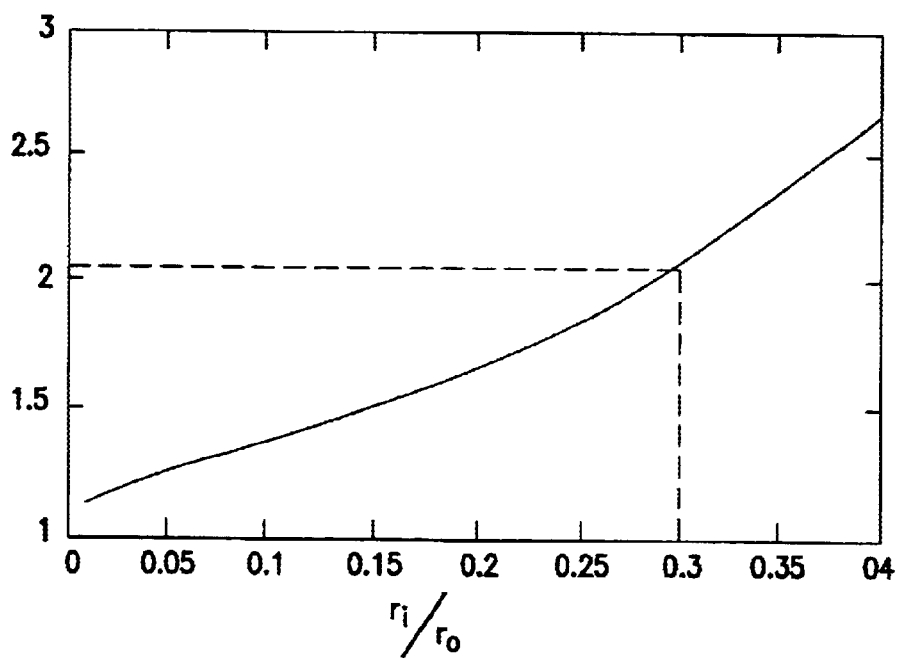
FIG. 3 is a graph illustrating the relative intimal shear as a function of the dimensions of the deflector relative to the dimensions of the artery.

The dependence of shear relative to the parameter Δ is shown in FIG. 3, in which there is shown on the ordinate the relative intimal shear and on the abscissa the ratio between the radius of the deflector and the radius of the artery. Taking for example a cylindrical deflector whose radius corresponds to about one-third the radius of the artery, the intimal shear is increased at the wall by a factor of 2. If as in the example mentioned above, the ratio between the radius of the deflector and that of the artery is one-third, the surface occupied by the deflector represents only about 11% of the cross-section of the artery and hence constitutes only a negligible resistance to blood flow, according to fluid mechanics.

Thanks to the presence of a cylindrical body at the center of the artery, giving rise to a deflection of the blood flow, the shear stress at the wall is significantly locally increased. This body, by reason of its dimensions, does not greatly decrease the blood flow.

Figure 4:
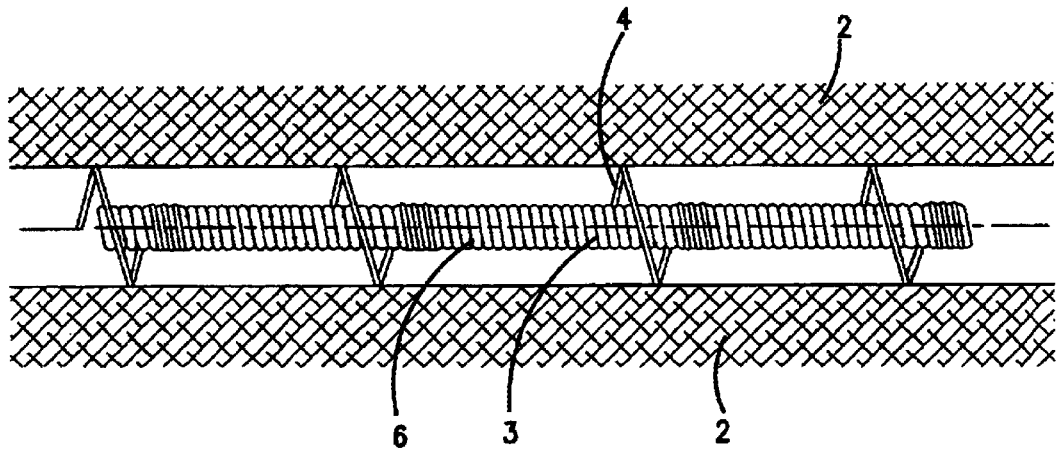
FIG. 4 is a side view of a stent according to the present invention.
Figure 5:
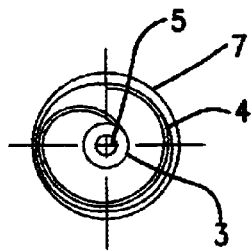
FIG. 5 is an end view of the stent shown in FIG. 4.

FIG. 4 shows a possible embodiment from among numerous variants, of a stent according to the present invention. This stent is in place in an artery or a vessel whose wall 2 has been schematically shown. It comprises a central portion 3 which fulfills the function of a flow deflector. This deflector 3 is made of a coil spring whose turns touch, in which each turn is connected to the adjacent turn for example by laser soldering. The solder points 6 are distributed along a spiral extending over all the length of the spring. Because of this, the deflector cannot deform along the longitudinal axis but nevertheless retains a certain flexibility, which facilitates its travel toward the region to be treated. At the two ends of the deflector 3, as well as at one or several points distributed over its length, small spirals 4 are soldered to the central deflector 3. These spirals 4 are radially expansible from a first diameter corresponding approximately to the diameter of the deflector 3, to a second larger diameter corresponding to the diameter of the artery. The spirals 4 bear, in the service position, on the internal walls 2 of the artery and have the same mechanical action on the wall as conventional auto-extensible stents. These spirals 4, once in contact with the arterial wall, maintain the deflector 3 in a centered position in the artery and avoid the latter from coming into contact with the annular wall of the artery. With reference to FIG. 5, there will be seen a passage 5 at the center of the deflector 3. This longitudinal passage 5, which extends over all the length of the deflector 3, permits mounting the stent at the end of an angioplasty catheter on a wire guide to facilitate its emplacement in the treated vessel. For the production of the spirals 4, there is preferably used a material which can be pre-stressed at a certain temperature and which resumes its original shape at a higher temperature. Nickel and titanium base alloys such as Nitinol (trademark) are perfectly adapted for the production of the spirals 4. Thus, during fabrication of the stent, the spirals 4 are cooled and hence become very malleable. They are then wound about the deflector 3. The stent is then emplaced in a catheter. During the emplacement of the stent, after separating the catheter from the stent, the spirals 4 reheat in contact with the blood and deploy radially to come into contact with the blood vessel wall. It follows that other known techniques in the field of auto-extensible stents can be used. The central deflector 3 can also be present in the form of solid cylindrical body provided with a central longitudinal bore, or be constituted by a hollow cylindrical body which can as the case may be serve as a reservoir for a substance to be administered in situ. Other modified embodiments of the deflector 3 are possible, in particular the use of several assembled elements such as a double spring for example. It is also possible to provide several flow deflectors 3 of smaller diameter and interconnected, for example three deflectors arranged at the summits of an isosceles triangle. So as not to disturb the blood flow in the vessel or the artery, there will be selected a ratio between the radius of the deflector 3 and that of the artery, lying between 0.1 and 0.8, preferably 0.3. To produce a stent according to the present invention, there will preferably be used biologically compatible material such as Nitinol (trademark) or stainless steel. It will be noted that certain copper alloys can also be envisaged using a suitable surface treatment, for example a polyester or TEFLON (trademark) coating.

To minimize the phenomenon of intimal hyperplasia, as has been mentioned in the introductory portion of the description, there is envisaged a local therapeutic action either by surface treatment permitting local distribution of an anti-restenosis substance, or by radiotherapy. These techniques can easily be applied to the stent according to the present invention. It thus suffices to provide a suitable surface treatment of the spirals 4 in contact with the arterial wall. The cumulative effect of an increase in shear stresses at the wall is thus combined with a radiotherapeutic or chemically therapeutic action. It will be noted that not only the portions directly in contact with the arterial wall can have suitable surface treatment, but also the deflector 3.

It is evident that the stent according to the present invention can have other shapes, the essential characteristic remaining in the presence of a flow deflector increasing the shear stress at the internal wall of the artery and maintained in position in the artery, preferably centered in this latter. In particular, the stent could have the form of a tubular body 7 open at its two ends and comprising at its center a cylindrical body 3 connected in a flexible manner to the external tubular body 7.

In certain cases, it is not desired to leave the stent permanently in the artery. To this end, certain stents are made of biodegradable materials. These materials can of course be used to make a stent according to the present invention.

The process which permits locally increasing the shear stress at the wall of a vessel or an artery comprises the following steps. There is introduced with a catheter and a wire guide an intravascular stent of the type described above to the diseased region of the artery to be treated. During the passage of the stent through the arterial system, this latter has a diameter approximately identical to that of the catheter. The stent is then emplaced by separating this latter from the catheter; during this operation, the spirals 4 of the stent extend radially and bear against the internal wall of the artery. Finally the catheter is withdrawn, then the wire guide.

It will further be noted that the stent which is the object of the present invention is easy to produce and can be packaged with a catheter, such that it is directly usable by the practitioner.

What is claimed is:

1. A blood flow deflector for introduction into an artery or blood vessel, comprising:
   a centrally located elongated body;
   resilient holding means attached to said elongated body, said holding means being expansible from a first diameter corresponding to a diameter of said elongated body to a second diameter corresponding to a diameter of a target artery or a blood vessel,
   said holding means bearing, in a service position, on an internal wall of the artery or blood vessel and maintaining said elongated body centered in the artery or the blood vessel,
   said elongated body being sized to locally increase the shear stress at least 50% at the internal wall by deflecting lines of blood flow in a radial direction while imposing minimal hemo dynamical resistance to flow,
   wherein a ratio between a radius of the elongated body over a radius of the resilient holding means in the service position is 0.3.

2. An intravascular implant adapted to be introduced into an artery or blood vessel, comprising:
   at least one blood flow deflector configured as a centrally located elongated body provided with resilient holding means expansible from a first diameter corresponding to a diameter of the elongated body to a second diameter corresponding to a diameter of a target artery or a blood vessel,
   said holding means bearing, in a service position, on an internal wall of the artery or the blood vessel and maintaining the elongated body centered in the artery or blood vessel,
   said elongated body being sized to locally increase the shear stress at the internal wall by deflecting lines of blood flow in a radial direction; and a tubular body open at two ends, the elongated body being centered within the tubular body and being connected to the tubular body by said holding means, wherein the elongated body of the blood flow deflector is constituted of a coil spring having a longitudinal interior passage mountable to an angioplasty catheter on a guide wire, wherein a ratio between a radius of the elongated body of the blood flow deflector over a radius of the holding means in the service position is 0.3.

3. The intravascular implant according to claim 2, wherein the holding means are constituted of at least two wire elements connected to the elongated body of the blood flow deflector at one of their ends.

4. The intravascular implant according to claim 2, wherein the blood flow deflector is made of a material having shape memory.

5. The intravascular implant according to claim 2, wherein the blood flow deflector comprises a radioactive isotope effective to reduce intimal hyperplasia of the arterial wall.

6. The intravascular implant according to claim 2, wherein the holding means and the elongated body of the flow deflector have a specific surface treatment permitting the diffusion of a substance having an action on the arterial wall.

7. The intravascular implant according to claim 2, wherein the elongated body is made of a biodegradable material.

8. The implant of claim 2, wherein the blood flow deflector is shaped to increase the shear stress along an entire length of the internal wall corresponding to a length of the blood flow deflector.

9. The stent of claim 2, wherein the wire elements are spirals.

10. A stent adapted to be introduced into an artery or a blood vessel, comprising:

at least one flow deflector (3) permitting deflecting the lines of current radially in the direction of walls of the artery or the blood vessel, thereby giving rise to a greater radial speed gradient adjacent the walls (2) which locally increases the shear stress on an internal wall of the artery or the blood vessel (2);

the flow deflector (3) being provided with a radially extensible holding means (4) bearing in the service position against the internal wall of the artery or the blood vessel (2), said radially extensible holding means (4) preventing the deflector (3) from coming into contact with the internal wall of the artery or the blood vessel and having a mechanical action to support the wall, wherein the deflector (3) comprises a spring rolled turn by turn in which each turn is connected to the following by a solder point (6) and the radially extensible holding means comprises at least two flexible radially extensible wire elements connected to the deflector (3) at one of their ends.

11. The intravascular implant according to claim 10, wherein the deflector comprises an elongated body and a ratio between a radius of the elongated body of the deflector over a radius of the holding means in the service position is between 0.1 and 0.8.

12. The intravascular implant according to claim 11, wherein the deflector comprises an elongated body and a ratio between a radius of the elongated body of the deflector over a radius of the holding means in the service position is 0.15 to 0.4.

13. The intravascular implant according to claim 10, wherein the blood flow deflector is made of a material having shape memory.

14. The intravascular implant according to claim 10, wherein the blood flow deflector comprises a radioactive isotope effective to reduce intimal hyperplasia of the arterial wall.

15. The intravascular implant according to claim 10, wherein the holding means and the elongated body of the flow deflector have a specific surface treatment permitting the diffusion of a substance having an action on the arterial wall.

16. The intravascular implant according to claim 10, wherein the elongated body is made of biodegradable material.

17. A stent for introduction into an artery or a blood vessel, comprising:

a blood flow deflector comprising a coil spring; and wires attached to the deflector at least at each of two ends of the deflector and along points between the two ends, the wires being radially expansible from a first diameter corresponding to a diameter of the deflector to a second larger diameter corresponding to a diameter of a target artery or blood vessel, the wires adapted to bear, in a service position, on an internal wall of the artery or blood vessel and to maintain the deflector centered in the artery or blood vessel, the coil spring having a longitudinal interior passage adapted to be mounted to an angioplasty catheter on a wire guide, and the deflector being sized to locally increase a shear stress at the internal wall by deflecting lines of flow in a radial direction, wherein the wires are soldered to the deflector, and a ratio between a radius of the coil spring over a radius of the wires in the service position is 0.3.

18. An intravascular implant adapted to be introduced into an artery or blood vessel, comprising:

at least one blood flow deflector configured as a centrally located elongated body provided with resilient holding means expansible from a first diameter corresponding to a diameter of the elongated body to a second diameter corresponding to a diameter of a target artery or a blood vessel, said holding means bearing, in a service position, on an internal wall of the artery or the blood vessel and maintaining the elongated body centered in the artery or blood vessel, said elongated body being sized to locally increase the shear stress at the internal wall by deflecting lines of blood flow in a radial direction, a tubular body open at two ends, the elongated body being centered within the tubular body and being connected to the tubular body by said holding means, wherein the elongated body of the blood flow deflector is constituted of a coil spring having a longitudinal interior passage adapted to be mounted to an angioplasty catheter on a guide wire, the holding means are constituted of at least two spiral wire elements connected to the elongated body of the blood flow deflector at one of their ends, and the spiral wires terminate at another of their ends in a line segment having a point end.

* * * * *